US010064982B2

(12) United States Patent
Roorda et al.

(10) Patent No.: US 10,064,982 B2
(45) Date of Patent: Sep. 4, 2018

(54) PDLLA STENT COATING

(71) Applicant: Abbott Cardiovascular Systems Inc., Santa Clara, CA (US)

(72) Inventors: Wouter E. Roorda, Palo Alto, CA (US); Ni Ding, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 14/832,889

(22) Filed: Aug. 21, 2015

(65) Prior Publication Data

US 2015/0359943 A1 Dec. 17, 2015

Related U.S. Application Data

(63) Continuation of application No. 14/259,458, filed on Apr. 23, 2014, now abandoned, which is a continuation of application No. 11/022,228, filed on Dec. 23, 2004, now Pat. No. 8,741,378, which is a continuation-in-part of application No. 09/894,293, filed on Jun. 27, 2001, now abandoned.

(51) Int. Cl.
*A61F 2/30* (2006.01)
*A61L 31/08* (2006.01)
*B05D 1/02* (2006.01)
*A61L 31/16* (2006.01)
*A61K 31/436* (2006.01)
*A61L 31/10* (2006.01)
*A61F 2/82* (2013.01)
*A61K 31/439* (2006.01)

(52) U.S. Cl.
CPC .............. *A61L 31/08* (2013.01); *A61F 2/82* (2013.01); *A61K 31/436* (2013.01); *A61K 31/439* (2013.01); *A61L 31/10* (2013.01); *A61L 31/16* (2013.01); *B05D 1/02* (2013.01); *A61F 2002/30062* (2013.01); *A61F 2002/30064* (2013.01); *A61L 2300/216* (2013.01); *A61L 2300/606* (2013.01); *A61L 2420/02* (2013.01); *A61L 2420/06* (2013.01)

(58) Field of Classification Search
CPC .... A61F 2002/3006; A61F 2002/30062; A61F 2002/30064; A61F 2002/30084; A61F 2210/004; A61F 2/82; A61F 2002/30535; A61F 2210/0019; A61F 2240/004; A61F 2/07; A61F 2/24; A61F 2210/0076; A61F 2/915; A61F 2002/91558; A61F 2002/91533; A61F 2/91; A61F 13/51478; A61L 31/08; A61L 31/16; A61L 2300/216; A61L 2300/606; A61L 2420/02; A61L 2420/06; A61L 31/10; A61K 31/436; B05D 1/002; B05D 1/02; B05D 3/0254; B05D 3/06; B05D 3/068; B05D 3/14
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 3,773,737 A | 11/1973 | Goodman et al. |
| 3,849,514 A | 11/1974 | Gray, Jr. et al. |
| 3,882,816 A | 5/1975 | Rooz et al. |
| 3,995,075 A | 11/1976 | Cernauskas et al. |
| 4,226,243 A | 10/1980 | Shalaby et al. |
| 4,329,383 A | 5/1982 | Joh |
| 4,343,931 A | 8/1982 | Barrows |
| 4,529,792 A | 7/1985 | Barrows |
| 4,560,374 A | 12/1985 | Hammerslag |
| 4,611,051 A | 9/1986 | Hayes et al. |
| 4,656,242 A | 4/1987 | Swan et al. |
| 4,733,665 A | 3/1988 | Palmaz |
| 4,800,882 A | 1/1989 | Gianturco |
| 4,865,879 A | 9/1989 | Finlay |
| 4,882,168 A | 11/1989 | Casey et al. |
| 4,886,062 A | 12/1989 | Wiktor |
| 4,931,287 A | 6/1990 | Bae et al. |
| 4,941,870 A | 7/1990 | Okada et al. |
| 4,977,901 A | 12/1990 | Ofstead |
| 5,019,096 A | 5/1991 | Fox, Jr. et al. |
| 5,100,992 A | 3/1992 | Cohn et al. |
| 5,112,457 A | 5/1992 | Marchant |
| 5,130,173 A | 7/1992 | Barten et al. |
| 5,133,742 A | 7/1992 | Pinchuk |
| 5,163,952 A | 11/1992 | Froix |
| 5,165,919 A | 11/1992 | Sasaki et al. |
| 5,219,980 A | 6/1993 | Swidler |
| 5,258,020 A | 11/1993 | Froix |
| 5,272,012 A | 12/1993 | Opolski |

(Continued)

FOREIGN PATENT DOCUMENTS

DE 42 24 401 1/1994
EP 0 301 856 2/1989

(Continued)

OTHER PUBLICATIONS

Anonymous, *Cardiologists Draw-Up the Dream Stent*, Clinica 710:15 (Jun. 17, 1996), http://www.dialogweb.com/cgi/document?req=1061848202959, printed Aug. 25, 2003 (2 pages).

Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).

Anonymous, *Rolling Therapeutic Agent Loading Device for Therapeutic Agent Delivery or Coated Stent* (Abstract 434009), Res. Disclos. pp. 974-975 (Jun. 2000).

Anonymous, *Stenting continues to dominate cardiology*, Clinica 720:22 (Sep. 2, 1996), http://www.dialogweb.com/cgi/document?reg=1061848017752, printed Aug. 25, 2003 (2 pages).

(Continued)

*Primary Examiner* — Seema Mathew
(74) *Attorney, Agent, or Firm* — Squire Patton Boggs (US) LLP

(57) ABSTRACT

An amorphous PDLLA stent coating for drug delivery is disclosed.

2 Claims, 1 Drawing Sheet

(56) References Cited

U.S. PATENT DOCUMENTS

| | | |
|---|---|---|
| 5,292,516 A | 3/1994 | Viegas et al. |
| 5,298,260 A | 3/1994 | Viegas et al. |
| 5,300,295 A | 4/1994 | Viegas et al. |
| 5,306,501 A | 4/1994 | Viegas et al. |
| 5,306,786 A | 4/1994 | Moens et al. |
| 5,328,471 A | 7/1994 | Slepian |
| 5,330,768 A | 7/1994 | Park et al. |
| 5,380,299 A | 1/1995 | Fearnot et al. |
| 5,417,981 A | 5/1995 | Endo et al. |
| 5,443,458 A | 8/1995 | Eury |
| 5,444,113 A * | 8/1995 | Sinclair ............... A61L 15/26 523/124 |
| 5,447,724 A | 9/1995 | Helmus et al. |
| 5,455,040 A | 10/1995 | Marchant |
| 5,462,990 A | 10/1995 | Hubbell et al. |
| 5,464,650 A | 11/1995 | Berg et al. |
| 5,485,496 A | 1/1996 | Lee et al. |
| 5,516,881 A | 5/1996 | Lee et al. |
| 5,558,900 A | 9/1996 | Fan et al. |
| 5,569,463 A | 10/1996 | Helmus et al. |
| 5,578,073 A | 11/1996 | Haimovich et al. |
| 5,584,877 A | 12/1996 | Miyake et al. |
| 5,605,696 A | 2/1997 | Eury et al. |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,624,411 A | 4/1997 | Tuch |
| 5,628,730 A | 5/1997 | Shapland et al. |
| 5,644,020 A | 7/1997 | Timmermann et al. |
| 5,649,977 A | 7/1997 | Campbell |
| 5,658,995 A | 8/1997 | Kohn et al. |
| 5,667,767 A | 9/1997 | Greff et al. |
| 5,670,161 A | 9/1997 | Healy et al. |
| 5,670,558 A | 9/1997 | Onishi et al. |
| 5,674,242 A | 10/1997 | Phan et al. |
| 5,679,400 A | 10/1997 | Tuch |
| 5,700,286 A | 12/1997 | Tartaglia et al. |
| 5,702,754 A | 12/1997 | Zhong |
| 5,711,958 A | 1/1998 | Cohn et al. |
| 5,716,981 A | 2/1998 | Hunter et al. |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,759,205 A | 6/1998 | Valentini |
| 5,776,184 A | 7/1998 | Tuch |
| 5,783,657 A | 7/1998 | Pavlin et al. |
| 5,788,979 A | 8/1998 | Alt et al. |
| 5,800,392 A | 9/1998 | Racchini |
| 5,820,917 A | 10/1998 | Tuch |
| 5,824,048 A | 10/1998 | Tuch |
| 5,824,049 A | 10/1998 | Ragheb et al. |
| 5,830,178 A | 11/1998 | Jones et al. |
| 5,837,008 A | 11/1998 | Berg et al. |
| 5,837,313 A | 11/1998 | Ding et al. |
| 5,849,859 A | 12/1998 | Acemoglu |
| 5,851,508 A | 12/1998 | Greff et al. |
| 5,854,376 A | 12/1998 | Higashi |
| 5,858,746 A | 1/1999 | Hubbell et al. |
| 5,865,814 A | 2/1999 | Tuch |
| 5,869,127 A | 2/1999 | Zhong |
| 5,873,904 A | 2/1999 | Ragheb et al. |
| 5,876,433 A | 3/1999 | Lunn |
| 5,877,224 A | 3/1999 | Brocchini et al. |
| 5,879,697 A | 3/1999 | Ding et al. |
| 5,879,713 A | 3/1999 | Roth et al. |
| 5,891,507 A | 4/1999 | Jayaraman |
| 5,902,875 A | 5/1999 | Roby et al. |
| 5,905,168 A | 5/1999 | Dos Santos et al. |
| 5,910,564 A | 6/1999 | Gruning et al. |
| 5,914,387 A | 6/1999 | Roby et al. |
| 5,919,893 A | 7/1999 | Roby et al. |
| 5,925,720 A | 7/1999 | Kataoka et al. |
| 5,932,299 A | 8/1999 | Katoot |
| 5,955,509 A | 9/1999 | Webber et al. |
| 5,958,385 A | 9/1999 | Tondeur et al. |
| 5,962,138 A | 10/1999 | Kolluri et al. |
| 5,971,954 A | 10/1999 | Conway et al. |
| 5,980,928 A | 11/1999 | Terry |
| 5,980,972 A | 11/1999 | Ding |
| 5,997,517 A | 12/1999 | Whitbourne |
| 6,010,530 A | 1/2000 | Goicoechea |
| 6,011,125 A | 1/2000 | Lohmeijer et al. |
| 6,015,541 A | 1/2000 | Greff et al. |
| 6,030,371 A | 2/2000 | Pursley et al. |
| 6,033,582 A | 3/2000 | Lee et al. |
| 6,034,204 A | 3/2000 | Mohr et al. |
| 6,042,875 A | 3/2000 | Ding et al. |
| 6,051,576 A | 4/2000 | Ashton et al. |
| 6,051,648 A | 4/2000 | Rhee et al. |
| 6,054,553 A | 4/2000 | Groth et al. |
| 6,056,993 A | 5/2000 | Leidner et al. |
| 6,060,451 A | 5/2000 | DiMaio et al. |
| 6,060,518 A | 5/2000 | Kabanov et al. |
| 6,080,488 A | 6/2000 | Hostettler et al. |
| 6,096,070 A | 8/2000 | Ragheb et al. |
| 6,099,562 A | 8/2000 | Ding et al. |
| 6,110,188 A | 8/2000 | Narciso, Jr. |
| 6,110,483 A | 8/2000 | Whitbourne et al. |
| 6,113,629 A | 9/2000 | Ken |
| 6,120,491 A | 9/2000 | Kohn et al. |
| 6,120,536 A | 9/2000 | Ding et al. |
| 6,120,788 A | 9/2000 | Barrows |
| 6,120,904 A | 9/2000 | Hostettler et al. |
| 6,121,027 A | 9/2000 | Clapper et al. |
| 6,129,761 A | 10/2000 | Hubbell |
| 6,136,333 A | 10/2000 | Cohn et al. |
| 6,143,354 A | 11/2000 | Koulik et al. |
| 6,153,252 A | 11/2000 | Hossainy et al. |
| 6,156,064 A | 12/2000 | Chouinard |
| 6,156,373 A | 12/2000 | Zhong et al. |
| 6,159,978 A | 12/2000 | Myers et al. |
| 6,165,212 A | 12/2000 | Dereume et al. |
| 6,172,167 B1 | 1/2001 | Stapert et al. |
| 6,177,523 B1 | 1/2001 | Reich et al. |
| 6,180,632 B1 | 1/2001 | Myers et al. |
| 6,203,551 B1 | 3/2001 | Wu |
| 6,211,249 B1 | 4/2001 | Cohn et al. |
| 6,214,901 B1 | 4/2001 | Chudzik et al. |
| 6,231,600 B1 | 5/2001 | Zhong |
| 6,239,124 B1 | 5/2001 | Zenke et al. |
| 6,240,616 B1 | 6/2001 | Yan |
| 6,242,063 B1 * | 6/2001 | Ferrera ............... A61L 29/049 428/35.2 |
| 6,245,753 B1 | 6/2001 | Byun et al. |
| 6,245,760 B1 | 6/2001 | He et al. |
| 6,248,129 B1 | 6/2001 | Froix |
| 6,251,136 B1 | 6/2001 | Guruwaiya et al. |
| 6,254,632 B1 | 7/2001 | Wu et al. |
| 6,258,121 B1 | 7/2001 | Yang et al. |
| 6,258,371 B1 | 7/2001 | Koulik et al. |
| 6,262,034 B1 | 7/2001 | Mathiowitz et al. |
| 6,270,788 B1 | 8/2001 | Koulik et al. |
| 6,277,449 B1 | 8/2001 | Kolluri et al. |
| 6,283,947 B1 | 9/2001 | Mirzaee |
| 6,283,949 B1 | 9/2001 | Roorda |
| 6,284,305 B1 | 9/2001 | Ding et al. |
| 6,287,628 B1 | 9/2001 | Hossainy et al. |
| 6,299,604 B1 | 10/2001 | Ragheb et al. |
| 6,306,176 B1 | 10/2001 | Whitbourne |
| 6,331,313 B1 | 12/2001 | Wong et al. |
| 6,335,029 B1 | 1/2002 | Kamath et al. |
| 6,344,035 B1 | 2/2002 | Chudzik et al. |
| 6,346,110 B2 | 2/2002 | Wu |
| 6,358,556 B1 | 3/2002 | Ding et al. |
| 6,358,567 B2 | 3/2002 | Pham et al. |
| 6,364,903 B2 | 4/2002 | Tseng et al. |
| 6,368,658 B1 | 4/2002 | Schwarz et al. |
| 6,379,381 B1 | 4/2002 | Hossainy et al. |
| 6,387,379 B1 | 5/2002 | Goldberg et al. |
| 6,395,326 B1 | 5/2002 | Castro et al. |
| 6,419,692 B1 | 7/2002 | Yang et al. |
| 6,451,373 B1 | 9/2002 | Hossainy et al. |

(56) References Cited

U.S. PATENT DOCUMENTS

| | | |
|---|---|---|
| 6,482,834 B2 | 11/2002 | Spada et al. |
| 6,494,862 B1 | 12/2002 | Ray et al. |
| 6,503,538 B1 | 1/2003 | Chu et al. |
| 6,503,556 B2 | 1/2003 | Harish et al. |
| 6,503,954 B1 | 1/2003 | Bhat et al. |
| 6,506,437 B1 | 1/2003 | Harish et al. |
| 6,524,347 B1 | 2/2003 | Myers et al. |
| 6,527,801 B1 | 3/2003 | Dutta |
| 6,527,863 B1 | 3/2003 | Pacetti et al. |
| 6,528,526 B1 | 3/2003 | Myers et al. |
| 6,530,950 B1 | 3/2003 | Alvarado et al. |
| 6,530,951 B1 | 3/2003 | Bates et al. |
| 6,534,112 B1 | 3/2003 | Bouchier et al. |
| 6,540,776 B2 | 4/2003 | Sanders Millare et al. |
| 6,544,223 B1 | 4/2003 | Kokish |
| 6,544,543 B1 | 4/2003 | Mandrusov et al. |
| 6,544,582 B1 | 4/2003 | Yoe |
| 6,555,157 B1 | 4/2003 | Hossainy |
| 6,558,733 B1 | 5/2003 | Hossainy et al. |
| 6,565,659 B1 | 5/2003 | Pacetti et al. |
| 6,572,644 B1 | 6/2003 | Moein |
| 6,585,755 B2 | 7/2003 | Jackson et al. |
| 6,585,765 B1 | 7/2003 | Hossainy et al. |
| 6,585,926 B1 | 7/2003 | Mirzaee |
| 6,605,154 B1 | 8/2003 | Villareal |
| 6,613,363 B1 * | 9/2003 | Li ..................... A23G 4/06 426/3 |
| 6,616,765 B1 | 9/2003 | Castro et al. |
| 6,623,448 B2 | 9/2003 | Slater |
| 6,625,486 B2 | 9/2003 | Lundkvist et al. |
| 6,645,135 B1 | 11/2003 | Bhat |
| 6,645,195 B1 | 11/2003 | Bhat et al. |
| 6,656,216 B1 | 12/2003 | Hossainy et al. |
| 6,656,506 B1 | 12/2003 | Wu et al. |
| 6,660,034 B1 | 12/2003 | Mandrusov et al. |
| 6,663,662 B2 | 12/2003 | Pacetti et al. |
| 6,663,880 B1 | 12/2003 | Roorda et al. |
| 6,666,880 B1 | 12/2003 | Chiu et al. |
| 6,673,154 B1 | 1/2004 | Pacetti et al. |
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,723,120 B2 | 4/2004 | Yan |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 7,220,755 B2 | 5/2007 | Betts et al. |
| 7,285,304 B1 * | 10/2007 | Hossainy ..................... A61F 2/91 427/2.24 |
| 7,431,959 B1 * | 10/2008 | Dehnad ..................... B05D 3/14 427/2.21 |
| 7,524,528 B2 | 4/2009 | Kodas et al. |
| 7,727,275 B2 | 6/2010 | Betts et al. |
| 7,807,211 B2 * | 10/2010 | Hossainy ..................... A61F 2/82 427/2.1 |
| 7,867,988 B2 | 1/2011 | Yan et al. |
| 7,901,451 B2 | 3/2011 | Savage et al. |
| 8,088,789 B2 | 1/2012 | Yan et al. |
| 8,182,890 B2 | 5/2012 | Zheng et al. |
| 8,252,046 B2 | 8/2012 | Shulze et al. |
| 8,252,047 B2 | 8/2012 | Savage et al. |
| 8,308,795 B2 | 11/2012 | Shulze et al. |
| 8,323,760 B2 | 12/2012 | Zheng et al. |
| 8,367,081 B2 | 2/2013 | Yan et al. |
| 8,404,641 B2 | 3/2013 | Yan et al. |
| 8,545,550 B2 | 10/2013 | Shulze et al. |
| 8,636,792 B2 | 1/2014 | Zheng et al. |
| 8,715,341 B2 | 5/2014 | Shulze et al. |
| 8,741,378 B1 * | 6/2014 | Roorda ..................... B05D 1/02 427/2.1 |
| 8,871,292 B2 | 10/2014 | Savage et al. |
| 8,952,123 B1 * | 2/2015 | Ding ..................... C08G 63/64 528/271 |
| 9,387,282 B2 | 7/2016 | Kleiner et al. |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 * | 6/2002 | Sirhan ..................... A61L 2/91 623/1.15 |
| 2002/0087123 A1 | 7/2002 | Hossainy et al. |
| 2002/0091433 A1 | 7/2002 | Ding et al. |
| 2002/0094440 A1 | 7/2002 | Llanos et al. |
| 2002/0111590 A1 | 8/2002 | Davila et al. |
| 2002/0120326 A1 | 8/2002 | Michal |
| 2002/0123801 A1 | 9/2002 | Pacetti et al. |
| 2002/0142039 A1 | 10/2002 | Claude |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0004564 A1 | 1/2003 | Elkins et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0125800 A1 | 7/2003 | Shulze et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2003/0236573 A1 * | 12/2003 | Evans ..................... A61L 27/12 623/23.58 |
| 2004/0018296 A1 | 1/2004 | Castro et al. |
| 2004/0029952 A1 | 2/2004 | Chen et al. |
| 2004/0030380 A1 | 2/2004 | Shulze et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |

(56) References Cited

U.S. PATENT DOCUMENTS

| | | |
|---|---|---|
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0167572 A1* | 8/2004 | Roth ............... A61B 17/11 606/219 |
| 2004/0197372 A1* | 10/2004 | Llanos ............. A61L 31/16 424/423 |
| 2005/0079470 A1* | 4/2005 | Rutherford ........ A61O 5/04 433/226 |
| 2005/0131008 A1 | 6/2005 | Betts et al. |
| 2006/0093771 A1* | 5/2006 | Rypacek ........... A61L 31/10 428/36.91 |
| 2006/0229711 A1 | 10/2006 | Yan et al. |
| 2006/0246108 A1* | 11/2006 | Pacetti ............. A61L 31/10 424/426 |
| 2007/0027554 A1* | 2/2007 | Biran ............... A61L 31/146 623/23.74 |
| 2007/0155010 A1* | 7/2007 | Farnsworth ........ A61L 27/18 435/399 |
| 2008/0091262 A1* | 4/2008 | Gale ................ A61L 31/10 623/1.38 |
| 2008/0177373 A1 | 7/2008 | Huang et al. |
| 2009/0036978 A1 | 2/2009 | Kleiner et al. |
| 2009/0110713 A1* | 4/2009 | Lim ................ A61L 31/06 424/423 |
| 2009/0228094 A1 | 9/2009 | Yan et al. |
| 2009/0291111 A1* | 11/2009 | Lim ................ A61L 31/10 424/423 |
| 2010/0086579 A1 | 4/2010 | Yan et al. |
| 2010/0104734 A1 | 4/2010 | Orosa et al. |
| 2010/0256746 A1* | 10/2010 | Taylor ............. A61K 31/435 623/1.42 |
| 2010/0291175 A1* | 11/2010 | Trollsas ........... A61L 31/06 424/423 |
| 2011/0097364 A1 | 4/2011 | Yan et al. |
| 2012/0071500 A1 | 3/2012 | Yan et al. |
| 2012/0071962 A1 | 3/2012 | Huang et al. |
| 2012/0187606 A1 | 7/2012 | Zheng et al. |
| 2012/0283391 A1* | 11/2012 | Venkatraman ...... A61L 17/06 525/411 |
| 2013/0150943 A1 | 6/2013 | Zheng et al. |
| 2013/0230571 A1 | 9/2013 | Yan et al. |
| 2013/0331927 A1* | 12/2013 | Zheng .............. A61F 2/82 623/1.19 |
| 2014/0242144 A1* | 8/2014 | Sudhir ............. A61K 31/436 424/425 |
| 2015/0217029 A1* | 8/2015 | Ding ............... A61L 31/10 424/422 |
| 2015/0306282 A1* | 10/2015 | Scanlon ........... A61L 31/14 623/1.11 |
| 2015/0342764 A1* | 12/2015 | Ramzipoor ........ A61L 31/148 623/1.16 |
| 2016/0263287 A1* | 9/2016 | Zhang .............. A61L 31/022 |
| 2016/0279303 A1* | 9/2016 | Zhang .............. A61L 31/06 |
| 2016/0303295 A1 | 10/2016 | Kleiner et al. |

FOREIGN PATENT DOCUMENTS

| | | |
|---|---|---|
| EP | 0 396 429 | 11/1990 |
| EP | 0 514 406 | 11/1992 |
| EP | 0 604 022 | 6/1994 |
| EP | 0 623 354 | 11/1994 |
| EP | 0 665 023 | 8/1995 |
| EP | 0 701 802 | 3/1996 |
| EP | 0 716 836 | 6/1996 |
| EP | 0 809 999 | 12/1997 |
| EP | 0 832 655 | 4/1998 |
| EP | 0 850 651 | 7/1998 |
| EP | 0 879 595 | 11/1998 |
| EP | 0 910 584 | 4/1999 |
| EP | 0 923 953 | 6/1999 |
| EP | 0950386 | 10/1999 |
| EP | 0 953 320 | 11/1999 |
| EP | 0 970 711 | 1/2000 |
| EP | 0 982 041 | 3/2000 |
| EP | 1 023 879 | 8/2000 |
| EP | 1 192 957 | 4/2002 |
| EP | 1 273 314 | 1/2003 |
| EP | 1 689 754 B1 | 8/2007 |
| EP | 1 796 754 B1 | 10/2009 |
| EP | 2 113 230 A2 | 11/2009 |
| EP | 1 518 517 B1 | 12/2009 |
| EP | 2417943 | 2/2012 |
| EP | 2 123 311 B1 | 4/2012 |
| EP | 1 490 125 B2 | 6/2012 |
| EP | 2578186 | 4/2013 |
| EP | 1 505 930 B1 | 7/2014 |
| EP | 1 852 437 B1 | 9/2014 |
| EP | 2 316 377 B1 | 11/2014 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |
| WO | WO 91/12846 | 9/1991 |
| WO | WO 94/09760 | 5/1994 |
| WO | WO 95/10989 | 4/1995 |
| WO | WO 95/24929 | 9/1995 |
| WO | WO 96/40174 | 12/1996 |
| WO | WO 97/10011 | 3/1997 |
| WO | WO 1997/035575 | 10/1997 |
| WO | WO 97/45105 | 12/1997 |
| WO | WO 97/46590 | 12/1997 |
| WO | WO 98/08463 | 3/1998 |
| WO | WO 98/17331 | 4/1998 |
| WO | WO 98/32398 | 7/1998 |
| WO | WO 98/36784 | 8/1998 |
| WO | WO 99/01118 | 1/1999 |
| WO | WO 99/38546 | 8/1999 |
| WO | WO 99/63981 | 12/1999 |
| WO | WO 00/02599 | 1/2000 |
| WO | WO 00/12147 | 3/2000 |
| WO | WO 00/18446 | 4/2000 |
| WO | WO 00/64506 | 4/2000 |
| WO | WO 2000/050007 | 8/2000 |
| WO | WO 00/62830 | 10/2000 |
| WO | WO 01/01890 | 1/2001 |
| WO | WO 01/15751 | 3/2001 |
| WO | WO 01/17577 | 3/2001 |
| WO | WO 01/45763 | 6/2001 |
| WO | WO 01/49338 | 7/2001 |
| WO | WO 01/51027 | 7/2001 |
| WO | WO 01/74414 | 10/2001 |
| WO | WO 2001/087368 | 11/2001 |
| WO | WO 02/03890 | 1/2002 |
| WO | WO 2002/007601 | 1/2002 |
| WO | WO 2002/018477 | 3/2002 |
| WO | WO 02/26162 | 4/2002 |
| WO | WO 02/34311 | 5/2002 |
| WO | WO 02/47731 A2 | 6/2002 |
| WO | WO 2002/047731 | 6/2002 |
| WO | WO 02/56790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |

(56) References Cited

FOREIGN PATENT DOCUMENTS

| WO | WO 03/082368 | 10/2003 |
|---|---|---|
| WO | WO 2003/090818 | 11/2003 |
| WO | WO 2004/000383 | 12/2003 |
| WO | WO 2004/009145 | 1/2004 |
| WO | WO 2004/026361 A1 | 4/2004 |
| WO | WO 2004/087045 | 10/2004 |
| WO | WO 2005/051449 | 6/2005 |
| WO | WO 2005/063319 | 7/2005 |
| WO | WO 2009/018227 A2 | 2/2009 |
| WO | WO 2009/108490 A2 | 9/2009 |
| WO | WO 2010/025406 A1 | 3/2010 |

OTHER PUBLICATIONS

Aoyagi et al., *Preparation of cross-linked aliphatic polyester and application to thermo-responsive material*, Journal of Controlled Release 32:87-96 (1994).
Barath et al., *Low Dose of Antitumor Agents Prevents Smooth Muscle Cell Proliferation After Endothelial Injury*, JACC 13(2):252A (Abstract) (Feb. 1989).
Barbucci et al., *Coating of commercially available materials with a new heparinizable material*, J. Biomed. Mater. Res. 25:1259-1274 (Oct. 1991).
Chung et al., *Inner core segment design for drug delivery control of thermo-responsive polymeric micelles*, Journal of Controlled Release 65:93-103 (2000).
Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).
Dichek et al., *Seeding of Intravascular Stents with Genetically Engineered Endothelial Cells*, Circ. 80(5):1347-1353 (Nov. 1989).
Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).
Forrester et al., *A Paradigm for Restenosis Based on Cell Biology: Clues for the Development of New Preventive Therapies*; J. Am. Coll. Cardio. 1991; 17(3):758-769.
Helmus, *Overview of Biomedical Materials*, MRS Bulletin, pp. 33-38 (Sep. 1991).
Herdeg et al., *Antiproliferative Stent Coatings: Taxol and Related Compounds*, Semin. Intervent. Cardiol. 3:197-199 (1998).
Huang et al., *Biodegradable Polymers Derived from Aminoacids*, Macromol. Symp. 144, 7-32 (1999).
Inoue et al., *An AB block copolymer of oligo(methyl methacrylate) and poly(acrylic acid) for micellar delivery of hydrophobic drugs*, Journal of Controlled Release 51:221-229 (1998).
Kataoka et al., *Block copolymer micelles as vehicles for drug delivery*, Journal of Controlled Release 24:119-132 (1993).
Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).
Levy et al., *Strategies for Treating Arterial Restenosis Using Polymeric Controlled Release Implants*, Biotechnol. Bioact. Polym. [Proc. Am. Chem. Soc. Symp.], pp. 259-268 (1994).
Liu et al., *Drug release characteristics of unimolecular polymeric micelles*, Journal of Controlled Release 68:167-174 (2000).
Marconi et al., *Covalent bonding of heparin to a vinyl copolymer for biomedical applications*, Biomaterials 18(12):885-890 (1997).
Matsumaru et al., *Embolic Materials for Endovascular Treatment of Cerebral Lesions*, J. Biomater. Sci. Polymer Edn 8(7):555-569 (1997).
Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).
Miyazawa et al., *Effects of Pemirolast and Tranilast on Intimal Thickening After Arterial Injury in the Rat*, J. Cardiovasc. Pharmacol., pp. 157-162 (1997).
Nordrehaug et al., *A novel biocompatible coating applied to coronary stents*, EPO Heart Journal 14, p. 321 (P1694), Abstr. Suppl. (1993).
Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).
Ozaki et al., *New Stent Technologies*, Progress in Cardiovascular Diseases, vol. XXXIX(2):129-140 (Sep./Oct. 1996).
Pechar et al., *Poly(ethylene glycol) Multiblock Copolymer as a Carrier of Anti-Cancer Drug Doxorubicin*, Bioconjugate Chemistry 11(2):131-139 (Mar./Apr. 2000).
Peng et al., *Role of polymers in improving the results of stenting in coronary arteries*, Biomaterials 17:685-694 (1996).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm by Bosentan, Novel Endothelin Receptor*; Chemical Abstract 125:212307 (1996).
van Beusekom et al., *Coronary stent coatings*, Coronary Artery Disease 5(7):590-596 (Jul. 1994).
Wilensky et al., *Methods and Devices for Local Drug Delivery in Coronary and Peripheral Arteries*, Trends Cardiovasc. Med. 3(5):163-170 (1993).
Yokoyama et al., *Characterization of physical entrapment and chemical conjugation of adriamycin in polymeric micelles and their design for in vivo delivery to a solid tumor*, Journal of Controlled Release 50:79-92 (1998).
Alt, Eckhard et al., "Inhibition of Neointima Formation After Experimental Coronary Artery Stenting: A New Biodegradable Stent Coating Releasing Hirudin and the Prostacyclin Analogue Iloprost," Circulation, 2000, 101, pp. 1453-1458.
Butany, J. et al., "Coronary artery stents: identification and evaluation," J Clin Pathol, 2005, 58, pp. 795-804.
Colombo, Antonio et al., "Selection of Coronary Stents," Journal of the American College of Cardiology, vol. 40, No. 6, 2002, pp. 1021-1033.
Diener, T. et al., "Biodegradable Drug Depots on Coronary Stents—Local Drug Delivery in Interventional Cardiology," Progress in Biomedical Research, vol. 8, No. 2, Jun. 2003, pp. 82-91.
Herrmann, R. et al., "Antithrombogenic Coating of Stents Using a Biodegradable Drug Delivery Technology," Thromb Haemost, 1999, 82, pp. 51-57.
Jain, Rajeev A., "The manufacturing techniques of various drug loaded biodegradable poly(lactide-co-glycolide) (PLGA) devices," Biomaterials, 21, 2000, pp. 2475-2490.
Middleton, John C. et al., "Synthetic biodegradable polymers as orthopedic devices," Biomaterials, 21, 2000, pp. 2335-2346.
Panyam, Jayanth et al., "Polymer degradation and in vitro release of a model protein from poly(D,L-lactide-co-glycolide) nano- and microparticles," Journal of Controlled Release, 92, 2003, pp. 173-187.
Pillai, Omathanu et al., "Polymers in drug delivery," Current Opinion in Chemical Biology 2001, 5, pp. 447-451.
Uhrich, Kathryn E. et al., "Polymeric Systems for Controlled Drug Release," Chem. Rev. 1999, 99, pp. 3181-3198.
Costa Jr et al., "Novolimus™-elulting coronary stent system", Interv. Cardiol. 2010, vol. 2, No. 5, pp. 645-649.
Degradable Polymers Principles and Applications 2nd Edition Edited by Gerald Scott; Kluwer Academic Publishers, 2002, pp. 321-329; ISBN 1-4020-0790-6.
Lee et al., "Synthesis and Degradation of End-Group-Functionalized Polylactide," Journal of Polymer Science: Part A: Polymer Chemistry, 2001, vol. 39, pp. 973-985.

* cited by examiner

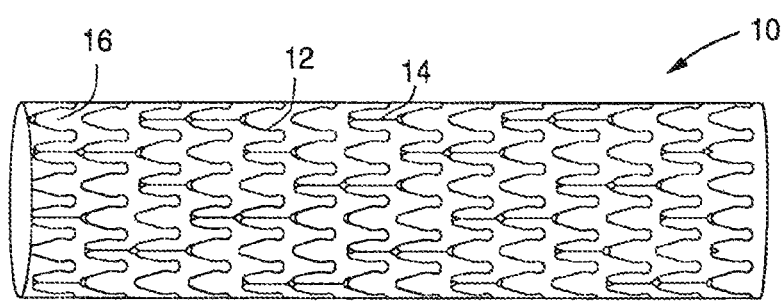
(PRIOR ART)

PDLLA STENT COATING

CROSS-REFERENCE

This application is a Continuation of application Ser. No. 14/259,458 filed on Apr. 23, 2014, which is a Continuation of application Ser. No. 11/022,228 filed Dec. 23, 2004, now U.S. Pat. No. 8,741,378, issued Jun. 3, 2014, which is a Continuation-In-Part of application Ser. No. 09/894,293 filed Jun. 27, 2001, which is abandoned, the entire contents of which are hereby incorporated by reference for all purposes.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of the passageway. Typically stents are capable of being compressed, so that they can be inserted through small lumens via catheters, and then expanded to a larger diameter once they are at the desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

FIG. 1 illustrates a conventional stent 10 formed from a plurality of struts 12. The plurality of struts 12 are radially expandable and interconnected by connecting elements 14 that are disposed between adjacent struts 12, leaving lateral openings or gaps 16 between adjacent struts 12. Struts 12 and connecting elements 14 define a tubular stent body having an outer, tissue-contacting surface and an inner surface.

Stents are used not only for mechanical intervention but also as vehicles for providing biological therapy. Biological therapy can be achieved by medicating the stents. Medicated stents provide for the local administration of a therapeutic substance at the diseased site. Local delivery of a therapeutic substance is a preferred method of treatment because the substance is concentrated at a specific site and thus smaller total levels of medication can be administered in comparison to systemic dosages that often produce adverse or even toxic side effects for the patient.

One method of medicating a stent involves the use of a polymeric carrier coated onto the surface of the stent. A composition including a solvent, a polymer dissolved in the solvent, and a therapeutic substance dispersed in the blend is applied to the stent by immersing the stent in the composition or by spraying the composition onto the stent. The solvent is allowed to evaporate, leaving on the stent strut surfaces a coating of the polymer and the therapeutic substance impregnated in the polymer.

A shortcoming of the above-described method of medicating a stent is the potential for coating defects due to the large amount of liquid composition applied to the relatively small surface area of the stent. The liquid composition can flow, wick, and collect as the amount of composition on the stent increases during the coating process. As the solvent evaporates, the excess composition hardens, leaving the excess coating as clumps or pools on the struts or webbing between the struts.

Another shortcoming of the above-described method of medicating a stent is the potential for loss of the therapeutic substance from the coating or production of a coating that does not provide for a suitable residence time of the substance at the implanted region. Initial portions of a liquid composition containing a therapeutic substance sprayed onto a stent adhere to the stent surface. However, as the liquid composition continues to be applied to the stent, layers of the composition are formed on top of one another. When exposed to the solvent in the upper layers, the therapeutic substance in the lower layers can be re-dissolved into the upper layers of the composition or extracted out from the coating. Having the therapeutic substance maintained in merely the upper regions of the coating provides for a short residence time of the substance at the implanted region, as the therapeutic substance will be quickly released. Prolonged residence times in situ may be desirable for a more effective treatment of a patient.

The present invention addresses such problems by providing methods of coating implantable devices.

SUMMARY

A stent is disclosed comprising a coating, the coating consisting of a poly(D,L-lactic acid) (PDLLA) and a macrocyclic drug, wherein the PDLLA has a degree of crystallinity of less than 20 percent, the measurement being by weight of the amount of polymer that is in the form of crystallites as measured by differential scanning calorimetry, wherein the coating has a thickness of 0.05 microns to 10 microns, and wherein the stent on which the coating is disposed is made from a bioabsorbably polymer.

BRIEF DESCRIPTION OF THE FIGURES

FIG. 1 illustrates a conventional stent.

DETAILED DESCRIPTION

This document incorporates by this reference the entire disclosure of U.S. patent application Ser. No. 09/894,293, which was filed on Jun. 27, 2001.

For ease of discussion, the methods detailed herein will be described with reference to coating a stent. However, the device or prosthesis coated in accordance with embodiments of the present invention may be any suitable medical substrate that can be implanted in a human or veterinary patient. Examples of such implantable devices include self-expandable stents, balloon-expandable stents, stent-grafts, grafts (e.g., aortic grafts)), artificial heart valves, cerebrospinal fluid shunts, pacemaker electrodes, and endocardial leads (e.g., FINELINE and ENDOTAK, available from Guidant Corporation). The underlying structure of the device can be of virtually any design. The device can be made of a metallic material or an alloy such as, but not limited to, cobalt chromium alloy (ELGILOY), stainless steel (316L), high nitrogen stain less steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In some embodiments, the implantable device is chosen to specifically exclude any one or any combination of self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation). In some embodiments, the implantable device is not a catheter. In some embodiments in which the implantable device can be chosen to be a catheter, the implantable device is chosen not to be a catheter liner.

The methods of some embodiments of the current invention comprise adjusting the temperature of an implantable portion of a medical device to a target temperature, which is always non-ambient, and then coating the implantable portion of the medical device with a coating substance. In some embodiments, adjusting occurs such that the increase or decrease in temperature only occurs before applying the coating substance begins. In other embodiments, adjusting occurs such that heating or cooling starts before and continues during the applying step or the adjusting and applying steps occur substantially together.

Different invention embodiments employ different "adjusting" profiles. For instance, in some profiles, the implantable device is adjusted to the target temperature before applying a coating substance and then applying occurs (with or without some amount of temperature decrease before crimping); alternatively, the implantable device is adjusted to the target temperature before applying a coating substance and maintained at or near the target temperature during applying; alternatively, applying is started, the implantable medical device is adjusted to the target temperature, and applying is completed. In some embodiments, applying begins before the implantable device has reached the target temperature and continues until or after the target temperature has been reached.

For purposes of this disclosure, ambient temperature is the temperature of the implantable device when it has not been purposely heated or cooled. In alternative embodiments, ambient temperature is room temperature, 25-30° C., 20-30° C., 20-25° C., 23-27° C. or 10-30° C. Similarly, for purposes of this disclosure, a target temperature is a temperature numerically different from ambient temperature. In some embodiments, the difference between the target temperature and ambient is brought about by purposely heating or cooling the implantable device.

A target temperature is chosen based on the characteristics of the components of the coating substance. For instance, if the solvent of the coating substance is non-volatile or has a low volatility, the target temperature can be chosen to be above ambient temperature to improve the evaporation rate. Conversely, if the coating substance solvent is volatile, the target temperature can be chosen to be below ambient temperature to lower the evaporation rate. The identity of the solvent is not the only characteristic upon which a target temperature can be based. For instance, if the coating substance comprises a therapeutic substance, the target temperature can be chosen to minimize thermal degradation of the therapeutic substance. Alternatively, if a polymer is used in the coating substance, the target temperature can be chosen above Tg of the polymer to improve its flow characteristics during deposition. In other embodiments, if the solvent of the coating substance has a high boiling point, the target temperature can be chosen to be above ambient temperature to improve the evaporation rate. Conversely, if the coating substance solvent has a low boiling point, the target temperature can be chosen to be below ambient temperature to lower the evaporation rate. Similarly, if the solvent is likely to freeze at ambient temperature during the applying step, the target temperature can be chosen to maintain it in a molten state to facilitate its removal. Those of ordinary skill in the art will be able to identify other characteristics of components of the coating substance that can be improved by applying the substances to an implantable device that is at a non-ambient target temperature.

In some embodiments, the target temperature is chosen to be above ambient temperature if the solvent is non-volatile or has low volatility. In some embodiments, non-volatile and having low volatility take their standard meanings as recognized by those of ordinary skill in the art. In these or other embodiments, nonvolatile and having low volatility means that the solvent has a volatility such that it does not substantially evaporate in a scientifically or commercially reasonable time as that time would be understood by one of ordinary skill in the art.

In some embodiments, non-volatile or having a low volatility means that when a solution composed of at least the solvent is applied to an implantable device the solvent does not substantially evaporate within 30 sec, 60 sec, 2 min, 5 min, 10 min, 15 min, 30 min, or 60 min at ambient temperature and pressure. In some embodiments, the target temperature is chosen to be below ambient temperature if the solvent is volatile. In some embodiments, volatile takes its standard meanings as recognized by those of ordinary skill in the art. In these or other embodiments, volatile means the solvent substantially evaporates fast enough to compromise the coating in a scientifically or commercially unreasonable manner as that would be understood by one of ordinary skill in the art. In some embodiments, volatile means that when a solution composed of at least the solvent is applied to an implantable device the solvent substantially evaporates within <30 sec, <20 sec, <15 sec, <10 sec, <8 sec, <5 sec, <4 sec, <3 sec, <2 see, or <1 sec at ambient temperature and pressure. In some embodiments, the target temperature is chosen to be below the decomposition region for a therapeutic substance.

In some embodiments that use coating substances to form primer layers, the target temperature can be chosen higher than ambient. In some embodiments that use coating substances to form topcoat layers, the target temperature can be chosen close to ambient or lower than ambient temperature.

In some embodiments, adjusting the temperature of the implantable device comprises adjusting the temperature to a target temperature and then letting the temperature fluctuate thereafter.

In some embodiments, adjusting the temperature of the implantable medical device to a target temperature means adjusting the temperature to within ±1° C., ±2° C., ±3° C., ±4° C., ±5° C., ±6° C., ±8° C., ±9° C., ±10° C., ±12° C., ±15° C., or ±20° C. of the target temperature before, during, or after the applying step begins.

"Adjusting" the temperature of the medical device comprises placing the object that is to have its temperature adjusted into thermal contact with a heat source. For purposes of this disclosure, thermal contact with a heat source means heat source arrangement vis-à-vis the object so that energy would flow or be carried from the heat source to the object. Thermal contact is a generic term at least encompassing an arrangement of the object such that radiation, conduction, or convection from the heat source would transfer energy. In some embodiments, thermal contact is defined to exclude any of radiation, conduction, convection, or any combination of these. Furthermore no invention embodiments use a convection oven or an ultrasound energy source.

In some embodiments, "maintained near the target temperature" means that the temperature of the implantable device, when it contacts the coating substance, is the same as the target temperature or within ±1° C., ±2° C., ±3° C., ±4° C., ±5° C., ±6° C., ±7° C., ±8° C., ±9° C., ±10° C., ±12° C., ±15° C., or ±20° C. of the target temperature.

In some embodiments, "maintained at the target temperature during the applying step" means keeping the temperature of the implantable device the same as the target temperature or within ±1° C., ±2° C., ±3° C., ±4° C., ±5° C., ±6° C., ±7° C., ±8° C., ±9° C., ±10° C., ±12° C., ±15° C., or ±20° C. of the target temperature.

The applying step forms a coating on an implantable medical device such as a stent; it is accomplished in some embodiments by spraying a composition onto the stent. A spray apparatus, such as EFD 780S spray device with VALVEMATE 7040 control system (manufactured by EFD Inc., East Providence, R.I.), can be used to apply the composition to the stent. EFD 780S spray device is an air-assisted external mixing atomizer. The composition is atomized into small droplets by air and uniformly applied to the stent surfaces. The atomization pressure can be maintained at a range of about 5 psi to about 20 psi. The droplet size depends on factors such as viscosity of the solution, surface tension of the solvent, and atomization pressure. Other types of spray applicators, including air-assisted internal mixing atomizers and ultrasonic applicators, can also be used for the application of the composition.

During the application of the composition, the stent can be rotated about the stent's central longitudinal axis. Rotation of the stent can be from about 0.1 rpm to about 300 rpm, more narrowly from about 1 rpm to about 10 rpm. By way of example, the stent can rotate at about 3 rpm. The stent can also be moved in a linear direction along the same axis. The stent can be moved at about 1 mm/second to about 12 min/second, for example about 6 mm/second, or for a minimum of at least two passes (i.e., back and forth past the spray nozzle).

The flow rate of the composition from the spray nozzle can be from about 0.01 mg/second to about 1.0 mg/second, more narrowly about 0.1 mg/second. Only a small percentage of the composition that is delivered from the spray nozzle is ultimately deposited on the stent. By way of example, when a composition is sprayed to deliver about 1 mg of solids, only about 100 micrograms or about 10% of the solids sprayed will likely be deposited on the stent. Multiple repetitions for applying the composition can be performed, wherein each repetition can be, for example, about 0.5 second to about 5 seconds in duration. In these or other embodiments, the steps can be repeated 2-100, 2-50, 30-100, 20-50, 50-100, or greater than 100 times. The amount of coating applied by each repetition can be about 1 microgram/cm$^2$ (of stent surface) to about 50 micrograms/cm$^2$, for example less than about 20 micrograms/cm$^2$ per 1-second spray.

Each repetition can be followed by removal of a significant amount of the solvent(s). The removal of the solvent(s) can be performed following a waiting period of about 0.1 second to about 5 seconds after the application of the coating composition so as to allow the liquid sufficient time to flow and spread over the stent surface before the solvent(s) is removed to form a coating. The waiting period is particularly suitable if the coating composition contains a volatile solvent, such as solvents having boiling points >130° C. at ambient pressure, since such solvents are typically removed quickly.

The applying step excludes immersing the temperature-adjusted implantable device into the coating substance.

Removal of the solvent(s) can be induced by the application of a warm gas. The application of a warm gas between each repetition prevents coating defects and minimizes interaction between the active agent and the solvent. Any suitable gas can be employed, examples of which include air or nitrogen. The temperature of the warm gas can be from about 25° C. to about 200° C., more narrowly from about 40° C. to about 90° C. The flow speed of the gas can be from about 0.5 feet$^3$/second (0.01 meters$^3$/second) to about 50 feet$^3$/second (1.42 meters$^3$/second), more narrowly about 2.5 feet$^3$/second (0.07 meters$^3$/second) to about 15 feet$^3$/second (0.43 meters$^3$/second). The gas can be applied for about 1 second to about 100 seconds, more narrowly for about 2 seconds to about 20 seconds. By way of example, warm gas applications can be performed at a temperature of about 60° C., at a flow speed of about 10 feet$^3$/second, and for about 10 seconds.

In one embodiment, the stent can be warmed to a temperature of from about 35° C. to about 80° C. prior to the application of the coating composition so as to facilitate faster removal of the solvent(s). The particular temperature selected depends, at least in part, on the particular active agent employed in the coating composition. By way of example, pre-heating of the stent prior to applying a composition containing actinomycin D should be performed at a temperature not greater than about 55° C. Pre-heating is particularly suitable for embodiments in which the solvent(s) employed in the coating composition has a high boiling point, i.e., volatile solvents having boiling points of, for example, >130° C. at ambient pressure (e.g., dimethylsulfoxide (DMSO), dimethylformamide (DMF), and dimethylacetamide (DMAC)).

Any suitable number of repetitions of applying the composition followed by removing the solvent(s) can be performed to form a coating of a desired thickness or weight. Excessive application of the polymer can, however, cause coating defects. In embodiments in which the coating composition contains a volatile solvent, a waiting period of from about 0.1 second to about 20 seconds can be employed between solvent removal of one repetition and composition application of the subsequent repetition so as to ensure that the wetting rate of the coating composition is slower than the evaporation rate of the solvent within the composition, thereby promoting coating uniformity.

Operations such as wiping, centrifugation, or other web clearing acts can also be performed to achieve a more uniform coating. Briefly, wiping refers to the physical removal of excess coating from the surface of the stent; and centrifugation refers to rapid rotation of the stent about an axis of rotation. The excess coating can also be vacuumed off of the surface of the stent.

In accordance with one embodiment, the stent can be at least partially pre-expanded prior to the application of the composition. For example, the stent can be radially expanded about 20% to about 60%, more narrowly about 27% to about 55%—the measurement being taken from the stent's inner diameter at an expanded position as compared to the inner diameter at the unexpanded position. The expansion of the stent, for increasing the interspace between the stent struts during the application of the composition, can further prevent "cob web" formation between the stent struts.

A final heat treatment can be conducted to remove essentially all of the solvent(s) from the composition on the stent. The heat treatment can be conducted at about 30° C. to about 200° C. for about 15 minutes to about 16 hours, more narrowly at about 50° C. to about 100° C. for about 1 hour to about 4 hours. By way of example, the heat treatment can be conducted at about 75° C. for 1 hour. The temperature of exposure should not adversely affect the characteristics of the active agent or of the coating. The heating can be conducted in an anhydrous atmosphere and at ambient pressure. The heating can, alternatively, be conducted under a vacuum condition. It is understood that essentially all of the solvent(s) will be removed from the composition but traces or residues can remain blended in the coating.

By way of example, and not limitation, the coating, referred to herein as the primary or reservoir coating, can have a thickness of about 0.05 microns to about 10 microns. The particular thickness of the coating is based on the type of procedure for which the stem is employed and the amount, if any, of active agent that is desired to be delivered. Applying a plurality of reservoir coating layers, containing the same or different active agents, onto the stent can further increase the amount of the active ingredient to be carried by the stent, without causing coating defects.

In accordance with one embodiment, the coating substance can include a solvent and a polymer dissolved in the solvent. The coating substance can also include active agents, radiopaque elements, or radioactive isotopes. Representative examples of polymers that can be used to coat a stent include ethylene vinyl alcohol copolymer (commonly known by the generic name EVOH or by the trade name EVAL), poly(hydroxyvalerate); poly(L-lactic acid); poly-caprolactone; poly(lactide-coglycolide); poly(hydroxybutyrate); poly(hydroxybutyrate-co-valerate); polydioxanone; polyorthoester; polyanhydride; poly(glycolic acid); poly(D, L-lactic acid); poly(glycolic acid-co-trimethylene carbonate); polyphosphoester; polyphosphoester urethane; poly (amino acids); cyanoacrylates; poly(trimethylene carbonate); poly(iminocarbonate); copoly(ether-esters) (e.g. PEO/PLA); polyalkylene oxalates; polyphosphazenes; biomolecules, such as fibrin, fibrinogen, cellulose, starch, collagen and hyaluronic acid; polyurethanes; silicones; polyesters; polyolefins; polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

In some embodiments, the polymer or the processing conditions of the method are selected such that the polymer is non-crystalline. A crystalline polymer is one in which upon analysis a detectable pattern may be observed when using conventional x-ray scattering techniques. Such conventional techniques are disclosed, for example, in "The Structure of Crystalline Polymers", Tadokoro, H. (Wiley Interscience, 1979). The degree of crystallinity of a polymer is the measurement by weight of the amount of polymer that is in the form of crystallites, as measured by differential scanning calorimetry. For purposes of this disclosure, a polymer that is noncrystalline has a degree of crystallinity of less than about 20 percent.

"Solvent" is defined as a liquid substance or composition that is compatible with the polymer and is capable of dissolving the polymer at the concentration desired in the composition. Examples of solvents include, but are not limited to, dimethylsulfoxide (DMSO), chloroform, acetone, water (buffered saline), xylene, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, isopropanol admixed with water, N-methyl pyrrolidinone, toluene, and combinations thereof.

The therapeutic agent can inhibit vascular, smooth muscle cell activity. More specifically, the therapeutic agent can aim at inhibiting abnormal or inappropriate migration or proliferation of smooth muscle cells to prevent, inhibit, reduce, or treat restenosis. The therapeutic agent can also include any substance capable of exerting a therapeutic or prophylactic effect in the practice of the present invention. Useful therapeutic agents can include therapeutic agents selected form antibiotics; anticoagulants; antifibrins; antiinflammatories; antimitotics; antineoplastics; antioxidants; antiplatelets; antiproliferatives; antithrombins; and their combinations. Other useful therapeutic agents include actinomycin D or derivatives and analogs thereof (manufactured by Sigma-Aldrich 1001 West Saint Paul Avenue, Milwaukee, Wis. 53233; or COSMEGEN available from Merck); dactinomycin; actinomycin IV; actinomycin $I_1$; actinomycin $X_1$; actinomycin $C_1$a paclitaxel; docetaxel; aspirin; sodium heparin; low molecular weight heparin; hirudin; argatroban; forskolin; vapiprost; prostacyclin; prostacyclin analogs; dextran; D-phe-pro-arg-chloromethylketone (synthetic antithrombin); dipyridarnole; glycoprotein IIb/IIIa platelet membrane receptor antagonist; recombinant hirudin; thrombin inhibitor (available from Biogen); 7E-3B® (an antiplatelet drug from Centocor); methotrexate; azathioprine; vincristine; vinblastine; fluorouracil; adriamycin; mutamycin; angiopeptin (a somatostatin analog from Ibsen); angiotensin converting enzyme inhibitors; CAPTOPRIL (available from Squibb); CILAZAPRIL (available from Hoffman-LaRoche); LISINOPRIL (available from Merck & Co., Whitehouse Station, N.J.); calcium channel blockers; Nifedipine; colchicinefibroblast growth factor (FGF) antagonists; histamine antagonist; LOVASTATIN (an inhibitor of HMG-CoA reductase, a cholesterol lowering drug from Merck &Co.); monoclonal antibodies (such as PDGF receptors); nitroprusside; phosphodiesterase inhibitors; prostaglandin inhibitor (available from Glazo); Seramin (a PDGF antagonist); serotonin blockers; thioprotease inhibitors; triazolopyrimidine (a PDGF antagonist); nitric oxide; alpha-interferon; genetically engineered epithelial cells; dexamethasone; estradiol; clobetasol propionate; cisplatin; insulin sensitizers; receptor tyrosine kinase inhibitors; carboplatin; Rapamycin; 40-O-(2-hydroxyl)ethyl-rapamycin, or a functional analog or structural derivative thereof; 40-O-(3-hydroxyl)propyl-rapamycin; 40-O-2-(2-hydroxyl)ethoxyethyl-rapamycin and their combinations.

Individual embodiments exist in which the therapeutic agent is selected to specifically exclude any one of or any combination of the therapeutic agents or therapeutic agent families described above.

Some invention embodiments comprise a therapeutic agent or therapeutic agent combination, and some require a therapeutic agent or combination of therapeutic agents. Of the therapeutic agents specifically listed above, some invention embodiments exclude a single or any combination of these therapeutic agents.

Examples of radiopaque elements include, but are not limited to, gold, tantalum, and platinum. An example of a radioactive isotope is $P^{32}$. Sufficient amounts of such substances may be dispersed in the composition such that the substances are not present in the composition as agglomerates or flocs.

The methods for coating an implantable device, such as a stent, according to embodiments of the present invention, can be used to create a multi-layer structure that can include any one or any combination of the following four layers:

(a) a primer layer;

(b) a drug-polymer layer (also referred to as "reservoir" or "reservoir layer") or a polymer-free drug layer; and (c) a topcoat layer, which is likewise drug containing or drug free.

(d) a finishing layer, for biocompatibility possessing biobeneficial properties.

In some embodiment, an optional primer layer can be formed prior to the primary or reservoir coating to increase the retention of the primary or reservoir coating on the surface of the stent, particularly metallic surfaces such as stainless steel. The primer layer can act as an intermediary adhesive tie layer between the surface of the device and a reservoir coating carrying an active agent, allowing for the quantity of the active agent to be increased in the reservoir coating.

To form an optional primer layer on the surface of the stent, an embodiment of the above-described composition that is free from active agents is applied to the surface of the stent. Ethylene vinyl alcohol copolymer, for example, adheres very well to metallic surfaces, particularly stainless steel. Accordingly, the copolymer provides for a strong adhesive tie between the reservoir coating and the surface of the stent. With the use of thermoplastic polymers such as, but not limited to, ethylene vinyl alcohol copolymer, polycaprolactone, poly(lactide-co-glycolide), and poly(hydroxybutyrate), the deposited primer composition should be exposed to a heat treatment at a temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of the stent. The prosthesis should be exposed to the heat treatment for any suitable duration of time that will allow for the formation of the primer layer on the surface of the stent and for the evaporation of the solvent employed. By way of example and not limitation, the optional primer layer can have a thickness of about 0.01 microns to about 2 microns. The application of the primary or reservoir coating should be performed subsequent to the drying of the optional primer layer.

In another embodiment, an optional diffusion barrier can be formed over a reservoir coating containing an active agent to help control the rate at which the active agent is released from the coated stent. An embodiment of the composition, free from any active agents, can be applied to a selected portion of the primary or reservoir coating subsequent to the drying of the reservoir coating. Application of the composition and evaporation of the solvent to form the diffusion barrier can be accomplished via embodiments of the above-described method of the present invention. The diffusion barrier can have a thickness of about 0.2 microns to about 10 microns. It is understood by one of ordinary skill in the art that the thickness of the diffusion barrier is based on factors such as the type of stent, the type of procedure for which the stent is employed, and the rate of release that is desired. As described above with reference to the primary or reservoir coating, a final heat treatment can be conducted to remove essentially all of the solvent(s) from the optional diffusion barrier.

Either of the four layers or any combination of them can be formed using invention methods.

EXAMPLES

The embodiments of the present invention will be illustrated by the following set forth examples, which are being given by way of illustration only and not by way of limitation. All parameters and data are not to be construed to unduly limit the scope of the embodiments of the invention.

Example 1

Four 8 mm Multi-Link TETRA stents (available from Guidant Corporation) were coated using embodiments of the method of the present invention. The stents were cleaned by sonication in water, followed by sonication in isopropanol. The steins were dried at 70° C. and plasma cleaned in an argon plasma chamber.

Each unexpanded stent was positioned on a mandrel such that the mandrel contacted the stent at its opposing ends. An EFD 780S spray device with VALVEMATE 7040 control system (manufactured by EFD Inc., East Providence, R.I.) was used to apply the coating compositions to the stents. The spray nozzle was adjusted to provide a distance from the nozzle tip to the outer surface of the stent of approximately 4.5 cm and a spray angle of approximately 90° relative to the horizontal stents. The atomization pressure was set to be maintained throughout the coating process at 20 psi.

Each stent was passed under the spray nozzle for about 2 seconds. A composition containing 2% (w/w) poly-n-butyl methacrylate (PBMA) 337K in cyclohexanone:ethyl acetate (1:1) was sprayed onto one stent. A composition containing 2% (w/w) PBMA 649K in cyclohexanone:ethyl acetate (1:1) was sprayed onto two stents. A composition containing 2% (w/w) PBMA 857K in cyclohexanone:ethyl acetate (1:1) was sprayed onto one stent. Each stent was rotated about the stent's central longitudinal axis at a speed of 3 rpm during coating. After a waiting period of 1 second following the application of the respective compositions, warm air of approximately 80° C. was directed from an air gun onto each stent for 15 seconds to remove most of the solvents. The spraying-blowing cycle was repeated to deposit thirty-four layers on each stent, with a wait time of 5 seconds between each cycle. The coated stent was allowed to dry for about 60 minutes under vacuum conditions in an oven at a temperature of about 70° C. Each of the four coated stents had a uniform, smooth coating. In addition, the stent sprayed with 2% (w/w) PBMA 857K in cyclohexanone:ethyl acetate (1:1) was submitted for a simulated use test and was found to have good mechanical properties, no cracking, and good coating adhesion.

Example 2

An 8 mm Multi-Link TETRA stent was coated using embodiments of the method of the present invention. The stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) quinoline yellow dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the coating composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1 second. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit forty layers on the stent, depositing about 300 micrograms of coating. The coated stent was allowed to dry for about 3 hours under vacuum conditions at a temperature of about 75° C. The coated stent had a uniform, smooth coating with an estimated dye content of about 130 micrograms or 43% of the total amount of coating deposited.

Example 3

An 8 mm Multi-Link TETRA stent was coated using embodiments of the method of the present invention. The stent was cleaned by placement in an ultrasonic bath of isopropyl alcohol solution for 15 minutes. The stent was dried and plasma cleaned in a plasma chamber.

A primer composition containing 2% (w/w) poly-n-butyl methacrylate (PBMA) was prepared. A reservoir composition containing 2% (w/w) PBMA and 2.7% (w/w) ethyl eosin dye in methanol:cyclohexanone (1:1) was also prepared. In addition, a diffusion barrier composition containing 2% (w/w) PBMA was prepared.

The unexpanded stent was positioned on a mandrel such that the mandrel contacted the stent at its opposing ends. An EFT) 780S spray device with VALVEMATE 7040 control system was used to apply the various compositions to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi. The stent was rotated about the stent's central longitudinal axis at a speed of 3 rpm during coating.

The primer composition was applied to the stent by passing the stent under the spray nozzle for about 0.75 second. Warm air of approximately 100° C. was directed from an air gun onto the stent for 8 seconds to remove most of the solvents and form a primer layer on the stent. The reservoir composition was then applied to the primered stent by passing the stent under the spray nozzle for about 0.75 second. Warm air of approximately 100° C. was directed from an air gun onto the stent for 4 seconds to remove most of the solvents. The spraying-heating cycle was repeated to deposit forty layers on the stent, depositing about 419 micrograms of the reservoir coating. The coated stent was allowed to dry for about 3 hours under vacuum conditions at a temperature of about 75° C. The barrier layer composition was then applied to the reservoir-coated stem by passing the stent under the spray nozzle for about 0.75 second. Warm air of approximately 100° C. was directed from an air gun onto the stent for 4 seconds to remove most of the solvents. The spraying-heating cycle was repeated to deposit about 70 micrograms of the diffusion barrier. The coated stent was allowed to dry overnight under vacuum conditions at a temperature of about 75° C. The coated stent had a uniform, smooth coating with an estimated dye content of about 224 micrograms or 53% of the total amount of coating deposited.

Example 4

An 8 mm Multi-Link TETRA stent was coated using embodiments of the method of the present invention. The stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) quinoline yellow dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1.5 second. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit 3 layers on the stent, depositing about 115 micrograms of coating. The coated stent was allowed to dry for about 3 hours under vacuum conditions at a temperature of about 75° C. The coated stent had a uniform, smooth coating with an estimated dye content of about 38 micrograms or 33% of the total amount of coating deposited.

Example 5

To determine the maximum amount of coating that could be deposited on an 8 mm stent without visible webbing, a Multi-Link TETRA stent was coated using the same coating composition and parameters as described in Example 4. The spraying-heating cycle was repeated until 790 micrograms of coating had been deposited on the stent, at which time no webbing was observed.

Example 6

An 8 mm Multi-Link TETRA stent was coated using embodiments of the method of the present invention. The stent was cleaned by placement in an ultrasonic bath of isopropyl alcohol solution for 15 minutes. The stent was dried and plasma cleaned in a plasma chamber.

A composition containing 2% (w/w) poly-n-butyl methacrylate (PBMA) and 2% (w/w) solvent blue dye in chloroform:cyclohexanone (9:1) was prepared.

The unexpanded stent was positioned on a mandrel such that the mandrel contacted the stent at its opposing ends. An EFD 780S spray device with VALVEMATE 7040 control system was used to apply the composition to the stent. The spray nozzle was adjusted to provide a distance from the nozzle tip to the outer surface of the stent of 1.25 inches (3.18 cm) and a spray angle of approximately 90° relative to the horizontal stent. The atomization pressure was set to be maintained throughout the coating process at 15 psi.

The stent was passed under the spray nozzle for about 1.5 seconds. The stent was rotated about the stent's central longitudinal axis at a speed of 3 rpm during coating. Warm air of approximately 100° C. was directed from an air gun onto the stent for 4 seconds to remove most of the solvents. The spraying-heating cycle was repeated to deposit about 130 micrograms of coating. The coated stent was allowed to dry for about 3 hours under vacuum conditions at a temperature of about 75° C. The coated stent had a uniform, smooth coating with a estimated dye content of about 85 micrograms or 66% of the total amount of coating deposited.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects (such as monomer type or gas flow rate) composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

What is claimed is:

1. A stent comprising a coating, the coating consisting of a poly(D,L-lactic acid) (PDLLA) and a macrocyclic drug, wherein the PDLLA has a degree of crystallinity of less than 20 percent, the measurement being by weight of the amount of polymer that is in the form of crystallites as measured by differential scanning calorimetry, wherein the coating has a thickness of 0.05 microns to 10 microns, and wherein the stent on which the coating is disposed is made from a bioabsorbable polymer.

2. The stent of claim 1, wherein the drug is rapamycin.

* * * * *